United States Patent
Taffa et al.

(10) Patent No.: US 10,463,375 B2
(45) Date of Patent: Nov. 5, 2019

(54) MULTIBAND LIGATION DEVICE

(71) Applicant: Horten Medical Pty Ltd, Leichhardt, New South Wales (AU)

(72) Inventors: Mark Taffa, Sydney (AU); Mark Profaca, Sydney (AU); Thomas Robert Croston, Sydney (AU); Daniel Thomas Shores, Sydney (AU); Richard Sokolov, Sydney (AU)

(73) Assignee: Horten Medical Pty Ltd., Leichhardt (AU)

( * ) Notice: Subject to any disclaimer, the term of this patent is extended or adjusted under 35 U.S.C. 154(b) by 0 days.

(21) Appl. No.: 16/066,055

(22) PCT Filed: Dec. 23, 2016

(86) PCT No.: PCT/AU2016/051288
§ 371 (c)(1),
(2) Date: Jun. 25, 2018

(87) PCT Pub. No.: WO2017/106933
PCT Pub. Date: Jun. 29, 2017

(65) Prior Publication Data
US 2019/0150930 A1    May 23, 2019

(30) Foreign Application Priority Data
Dec. 23, 2015 (AU) ................... 2015905345

(51) Int. Cl.
*A61B 17/12* (2006.01)
(52) U.S. Cl.
CPC ............... *A61B 17/12009* (2013.01); *A61B 2017/12018* (2013.01)

(58) Field of Classification Search
CPC .............. A61B 17/12; A61B 17/12009; A61B 17/12013; A61B 2017/12004; A61B 2017/12018
See application file for complete search history.

(56) References Cited

U.S. PATENT DOCUMENTS

| 3,989,049 A | 11/1976 | Yoon |
| 4,493,319 A | 1/1985 | Polk et al. |

(Continued)

FOREIGN PATENT DOCUMENTS

| DE | 198 34 263 A1 | 2/2000 |
| EP | 1 952 770 A1 | 8/2008 |

OTHER PUBLICATIONS

ISA/AU, international Search Report and Written Opinion issued in International Application No. PCT/AU2016/051288, dated Feb. 13, 2017, 10 pages.

(Continued)

*Primary Examiner* — Todd J Scherbel
(74) *Attorney, Agent, or Firm* — Mauriel Kapouytian Woods LLP; Serge Krimnus

(57) ABSTRACT

An elastic band ligation device for the treatment of haemorrhoids, comprising an inner tube (60), a deployer (40), and a grasper (26), the grasper including at least two gripping arms (23) and slidably mounted within the inner tube (60) to open and close the gripping arms. In a closed position, retaining a haemorrhoid, the gripping arms are within the body, and the deployer is positioned to release one of a plurality of ligation bands (50). The grasper handle (31) and the deployer trigger (62) are operable by a single hand. Preferably the device is disposable and the deployer includes a ratchet so that it may only be moved forward towards the bands. In an alternative device (FIGS. 12-13), the body (20, 120) is moved to close the gripping arms.

12 Claims, 14 Drawing Sheets

(56) References Cited

U.S. PATENT DOCUMENTS

| | | | |
|---|---|---|---|
| 4,990,152 A | 2/1991 | Yoon | |
| 6,547,798 B1 | 4/2003 | Yoon et al. | |
| 7,037,314 B2 * | 5/2006 | Armstrong | A61B 1/31 606/1 |

OTHER PUBLICATIONS

IPEA/AU, International Preliminary Report on Patentability issued in International Application No. PCT/AU2016/051288, dated Dec. 6, 2017, 50 pages.

* cited by examiner

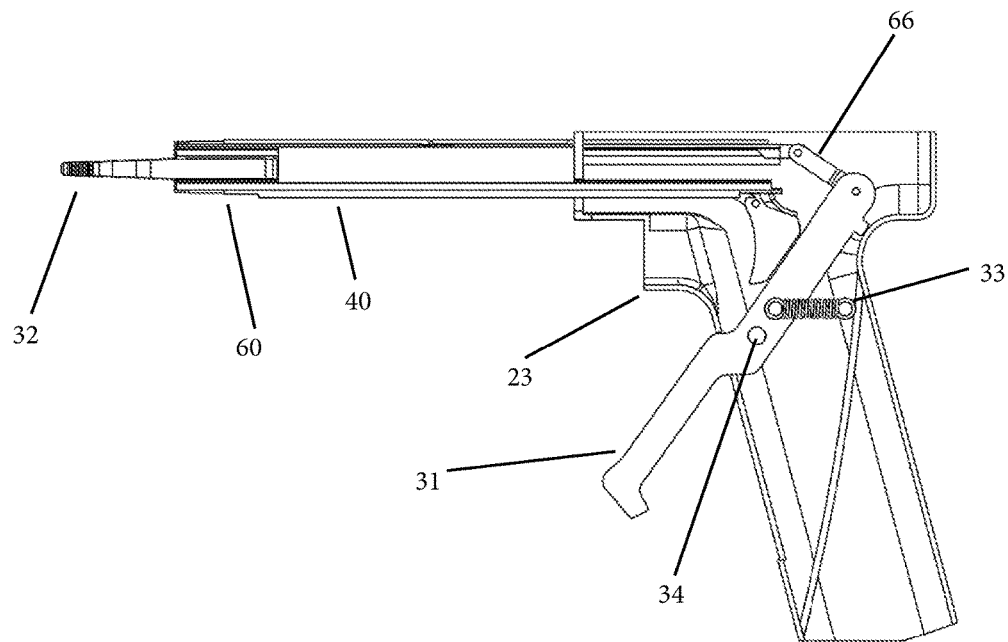
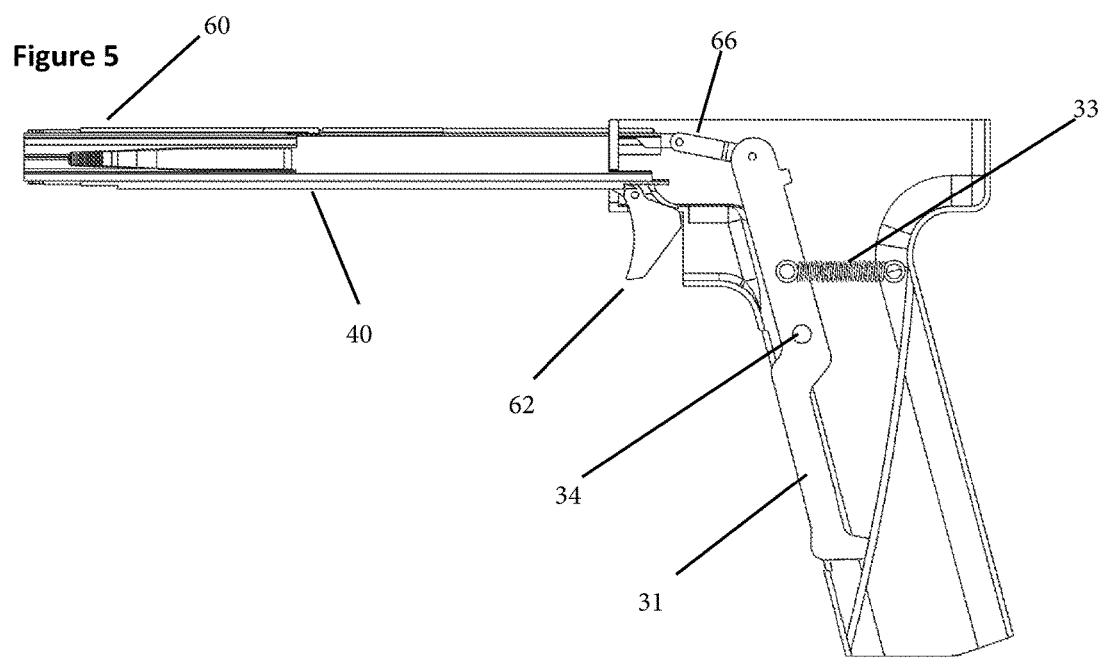
Figure 5
Figure 6

MULTIBAND LIGATION DEVICE

TECHNICAL FIELD

The present invention relates to devices and methods for performing ligation of haemorrhoids.

BACKGROUND OF THE INVENTION

Haemorrhoids are a common medical condition, in which vascular structures in the anal canal become swollen or inflamed. Internal haemorrhoids usually present with painless rectal bleeding, while external haemorrhoids may produce few symptoms or if thrombosed significant pain and swelling in the area of the anus. The present invention is concerned with the treatment of internal haemorrhoids.

One treatment for internal haemorrhoids is elastic band ligation. In this procedure, elastic bands are applied onto an internal haemorrhoid to cut off its blood supply. Within 5-7 days, the withered haemorrhoid falls off. It is common for several haemorrhoids to be ligated in the same procedure, and some practitioners prefer to apply two bands per haemorrhoid.

Many different types and combinations of devices are known. For example, the McGivney haemorrhoidal ligator uses a combination of re-usable instruments. It requires (at least) two handed operation, mechanical gripping of the haemorrhoid, and can be loaded with only one band at a time.

Disposable multiband dispensing devices, are available commercially. They are very effective, however, they require that suction be available. Whilst suction systems are routinely present in hospitals, they are not generally available in medical practitioner's rooms. Hand pumped suction based devices have been developed, for example the CRH O'Regan system. However, this is only able to dispense a single band.

U.S. Pat. No. 5,158,563 to Cosman discloses an instrument combining a ligator with a conventional set of forceps. It allows for only a single band to be mounted, and is taught to be integrated with the endoscope via a track.

It is an object of the present invention to provide a multiband dispensing ligature device which does not require the provision of suction.

SUMMARY OF THE INVENTION

In a first broad form, the present invention provides a multiband ligature device, which mechanically grasps the haemorrhoid for ligation, and can deploy a single band from a multi-band deployer, and which allows for single hand operation of the grasper and deployer.

According to one aspect, the present invention provides an elastic band ligation device, including a body, an inner tube, a deployer, and a grasper, the grasper including at least two gripping arms, the grasper being slidably mounted within the inner tube, so that movement of the grasper relative to the inner tube causes the gripping arms to open and close, the arrangement being such that when the gripping arms are in a closed position, and operatively retaining a haemorrhoid, the gripping arms are within the body, and the deployer is positioned to release a band around the haemorrhoid.

According to another aspect, the present invention provides an elastic band ligation device, including a body, a deployer, and a grasper, the grasper being operatively adapted to hold and retain a haemorrhoid under control of the handle, the deployer including a trigger adjacent the handle, the device being adapted to hold a plurality of bands in a position around the retained haemorrhoid, and the deployer being adapted to release a single band around the haemorrhoid upon operation of the trigger.

According to a further aspect, the present invention provides a manually operated elastic band ligation device, including a grasper for mechanically grasping a haemorrhoid, a deployer for retaining and selectively releasing a band around the grasped haemorrhoid, the grasper and the deployer being integrated into a single device, so that the grasper and deployer may be used by the operator with a single hand.

Appropriate implementations of the present invention accordingly permit simple, one-handed operation of a disposable ligature device, without any need for suction. The device may designed for single use, enhancing the safety of the procedure and making it more cost effective.

BRIEF DESCRIPTION OF THE DRAWINGS

Implementations of the present invention will now be described with reference to the figures, in which:

FIG. 5 is a detailed cross section view illustrating the first embodiment with the grasper open;

FIG. 6 is a detailed cross section view illustrating the first embodiment with the grasper closed;

DETAILED DESCRIPTION OF THE INVENTION

The present invention will be described primarily with reference to specific implementations, as shown in the accompanying figures. However, it will be understood that there are many alternative implementations of the present invention, and the examples shown and described are intended to be illustrative and not limitative.

It will be appreciated that the illustrative implementation is intended to be used to carry out an otherwise conventional ligature procedure, using a conventional anoscope to facilitate access, and with expected outcomes comparable to those of existing instruments. However, the implementation described below allows for a ligature device to be provided, with single handed operation, and without requiring the provision of a source of suction.

In a suitable implementation, such as the one described below in detail, the device may be a low cost, single use device which can be produced at a modest manufactured cost. Thus, such implementations allow for the cost effective use of a disposable instrument in this procedure, without requiring any special facilities at the place of treatment.

However, other implementations of the present invention could be made of more durable materials (with suitable modifications), for example stainless steel, as a reusable device. In further implementations, the device could combine a durable, reusable component with disposable, single use components.

There are several steps in a haemorrhoid banding procedure, whether using the device of the present invention or in a conventional procedure. An anoscope is introduced to the patient to facilitate access to the affected area. The haemorrhoid is then grasped by forceps, suction or otherwise, so as to be drawn gently outwards. A band is then placed around the base of the haemorrhoid. Some practitioners apply two bands per haemorrhoid. It is common to treat multiple haemorrhoids in the same procedure.

The band acts to cut off the blood supply to the haemorrhoid, so that it withers and typically falls off within 5-7 days.

Figure 1:
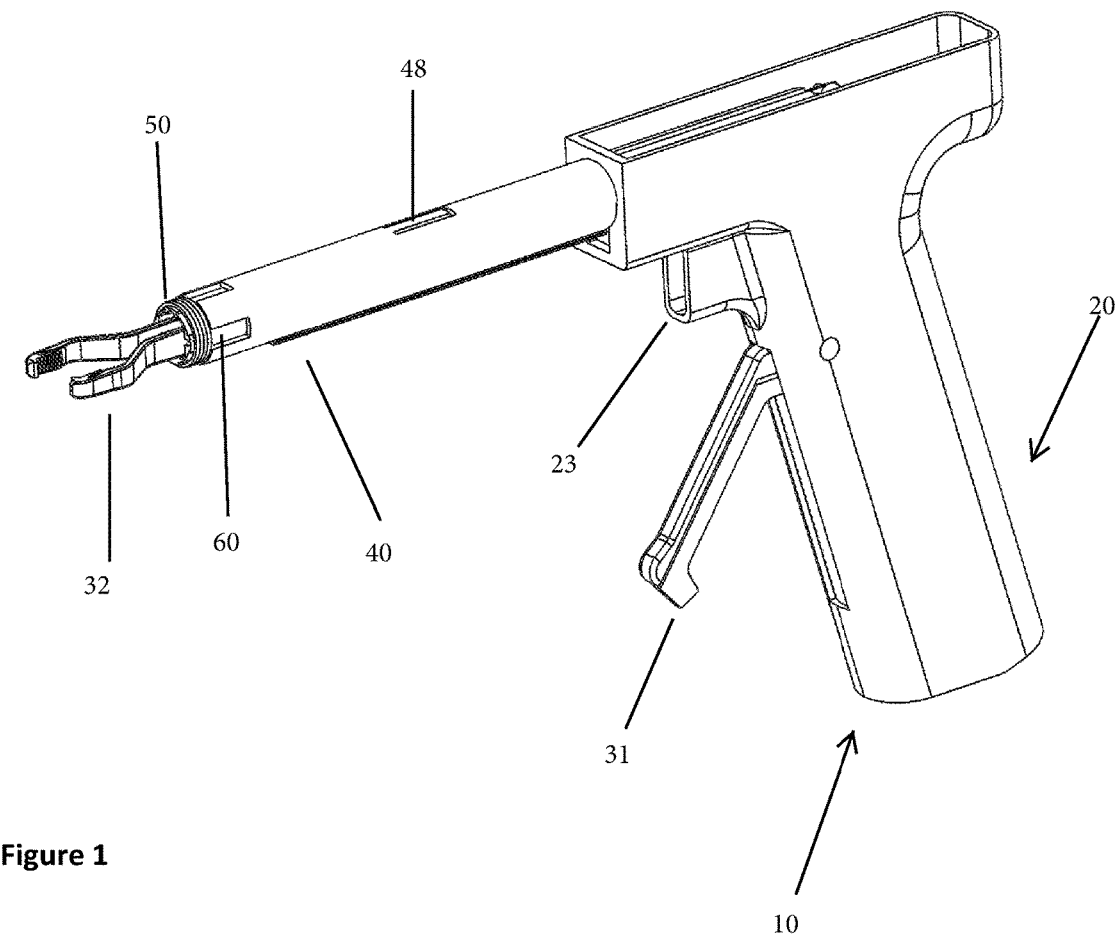
FIG. 1 is isometric view of a first embodiment of the present invention.

Referring to FIG. 1, this implementation of the ligation device 10 can be seen, with a handle 20, and grasper 32. Device 10 also includes inner tube 60 and outer tube 40, with bands 50 for use mounted on the end of tube 60. Grasper actuator 31 operates grasper 32, by moving inner tube 60 outwards to close grasper 32, as will be described in more detail below. Shroud 23 can be seen, from which trigger 62 (not visible in this view) protrudes in an operative state.

Figure 2:
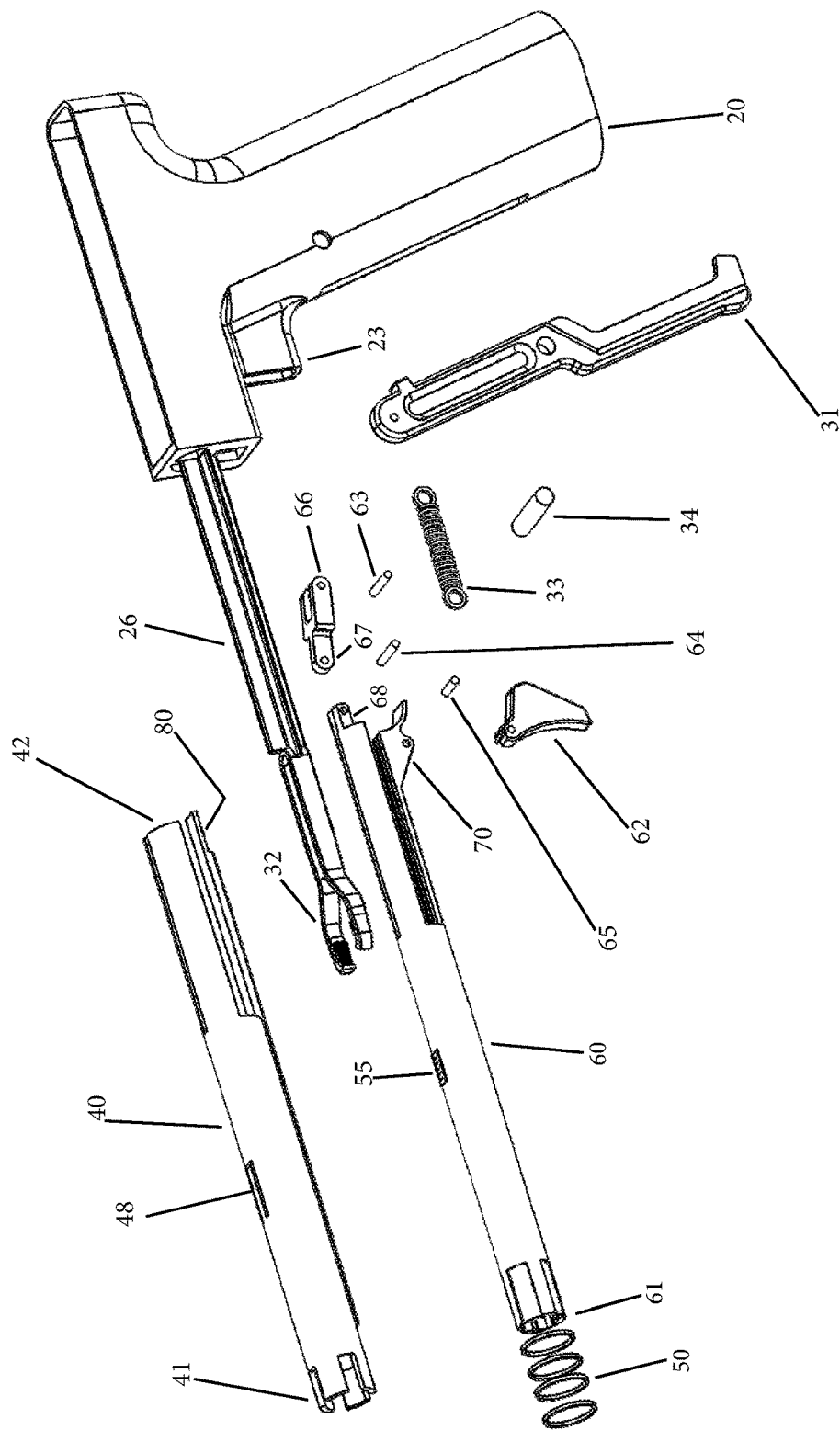
FIG. 2 is an exploded view of the first embodiment of the present invention.

FIG. 2 is an exploded view of the device of FIG. 1. It can be seen that grasper 32 is integral with the handle 20, and is connect via member 26. This direct connection allows the operator to precisely position grasper 32 as required, with a direct and positive connection to handle 20.

Inner tube 60 at one end has tip 61, with bands 50 loaded near the tip in use. Teeth 55 assist in the band deployment, as will be explained below. At the other end, projection 70 forms part of the mechanism, including spring 72, for trigger 62. Trigger 62 is connected via pin 65 to tube 60. Projection 68 connects tube 60 to link 67 via pin 64.

Link 67 connects in turn via trunnion 66 to handle 31, via pin 63. Handle 31 is pivotally mounted on handle 20 via pin 34, and retained in a biased position by spring 33.

It can therefore be seen that depressing handle 31 causes inner tube 60 to move outward, relative to handle 20, and therefore to close grasper 32.

Outer tube 40 includes, at one end, a leading edge 41, operative to deploy bands as will be explained below. The other end 42 includes ratchet teeth 80, which interact with the trigger 62 to allow movement of outer tube 40 and thereby deploy bands.

Figure 3:
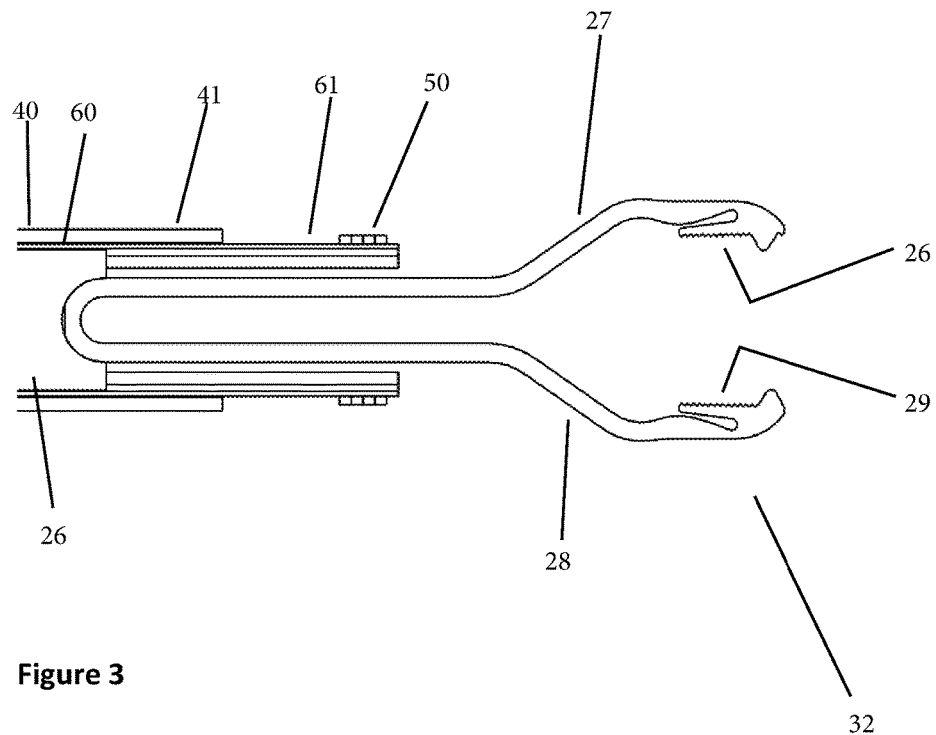
FIG. 3 is a view in cross section of a detail of an open grasper according to FIG. 1.
Figure 4:
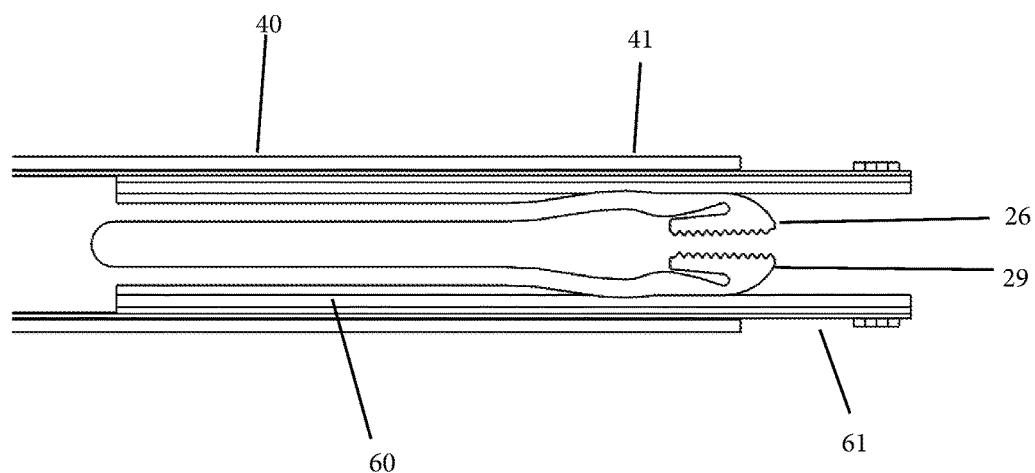
FIG. 4 is a view in cross section of a detail of a closed grasper according to FIG. 1.

FIGS. 3 and 4 illustrates the grasper head 32 in detail. Arms 27, 28 each have a respective grip surface 26, 29. The resilience of the arms provides the gripping force for gripping the haemorrhoid, as well as providing a degree of accommodation to the grasping action, allowing for some resilient movement of the grip surfaces 26,29. In FIG. 3, the grasper 32 can be seen projecting beyond inner tube 60 and the end 41 of outer tube 40. The tip 61 has 4 bands 50 loaded. In this position, the grasper is open and ready for the operator to grasp a haemorrhoid.

In FIG. 4, the operator has operated handle 31 (not visible in this view), so that inner tube 60, carrying with it outer tube 40, has translated forward relative to the grasper 32. Arms 27, 28 have therefore been forced the tip 61 of inner tube 60 to close, and to move inside inner tube 60. Grasper 32 is therefore in a closed position, with the arms inside inner tube 60. It will be understood that the material, length, and cross sectional shape of arms 27,28 may be varied in order to control the desired stiffness and responsiveness of the grasper 32, as well as the degree of closure to be achieved by the grip surfaces 26, 29.

FIG. 5 illustrates the implementation of FIG. 1, in section. The grasper 32 is open, and in the condition that it would be prior to insertion into an anoscope to carry out a ligature procedure. Handle 31 is forward, biased back by spring 33. As described above, handle 31 via link 66 connects to inner tube 60.

In FIG. 6, handle 31 has been urged backward by the operator. As handle 31 pivots on pin 34, it forces link 66 and hence inner tube 60 forward, closing grasper 32, as shown in FIG. 4. It can be seen that trigger 62, for deploying bands, is then exposed and available for use, so that the operator can deploy bands 50 around a haemorrhoid.

Figure 7:
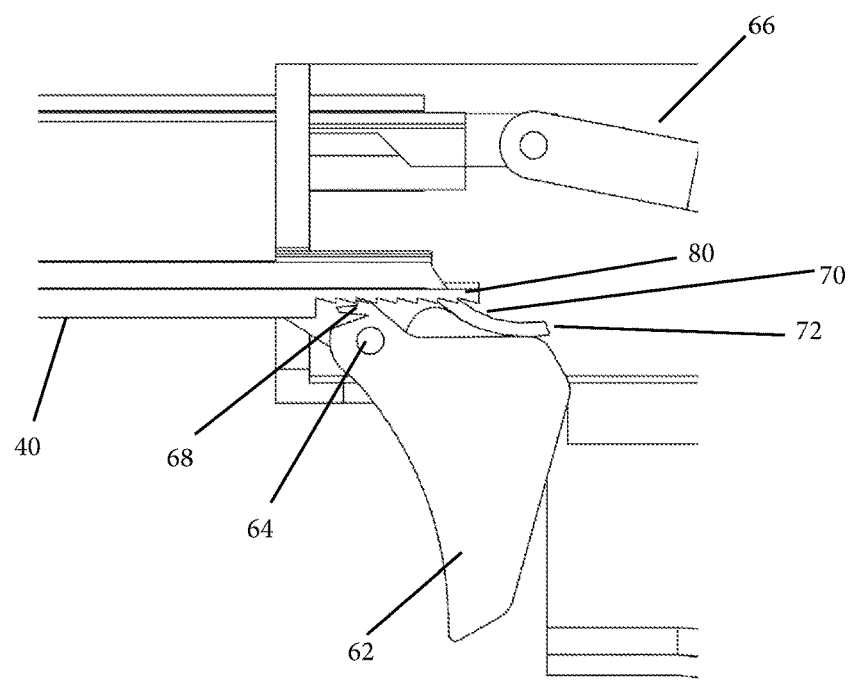
FIG. 7 is a detailed view of one implementation of the trigger mechanism for releasing bands.

FIG. 7 is a detail of the trigger mechanism, responsible for moving outer tube 40 relative to inner tube 60, so as to deploy bands from tip 61. It has been determined by the inventors that it is preferable that the bands are set back a distance from the very end of tip 61, so that they do not interfere with placement of the device or accidentally deploy during insertion of the device into an anoscope. The general mechanism is that the rearmost band is pushed by leading edge 41, and this transfers through the other bands, for example 4 in total, until the end most band is pushed from the end of tip 61 by leading edge 41, via the other bands.

One complication is that if the bands are set back from tip 61, the first band needs to be moved a different distance to be deployed relative to the other bands. This creates a complication for the trigger mechanism, which is operative to move outer tube 40 relative to inner tube 60. Of course, in other implementations, this may not be required, and other mechanisms may be used. It will be appreciated that the deployment mechanisms illustrated are examples only, and that any other suitable arrangements could be used. For example, whilst rectilinear section bands are shown, in other implementations round bands could be used. The mechanism's behaviour is also necessarily controlled by the material and physical characteristics of the material from which the bands are formed, how this interacts with the material of the tip 61, and other related issues as will be understood by those skilled in the art. It will be appreciated that while a specific band deployment mechanism at the tip is discussed, the present invention could be implemented with an alternative band dispensing arrangement.

The general intention with band deployment is to allow the operator to deploy a single band at a time. In some cases, it may be preferred to deploy more than one band on each haemorrhoid, but these are deployed one at a time. The mechanism described below deploys one band for each time the trigger is fully depressed, and when the trigger is released, it is reset to deploy the next band.

FIG. 7 shows trigger 62, which is pivotally mounted on pin 64, to projection 70 on inner tube 60. Projection 70 includes spring 72, which biases trigger 62 into the forward position. Trigger 68 also includes tooth 68, which engages ratchet teeth 80 on outer tube 40. Thus, as trigger 62 is pressed backwards, it drives outer tube 40 outward relative to inner tube 60.

Figure 31:
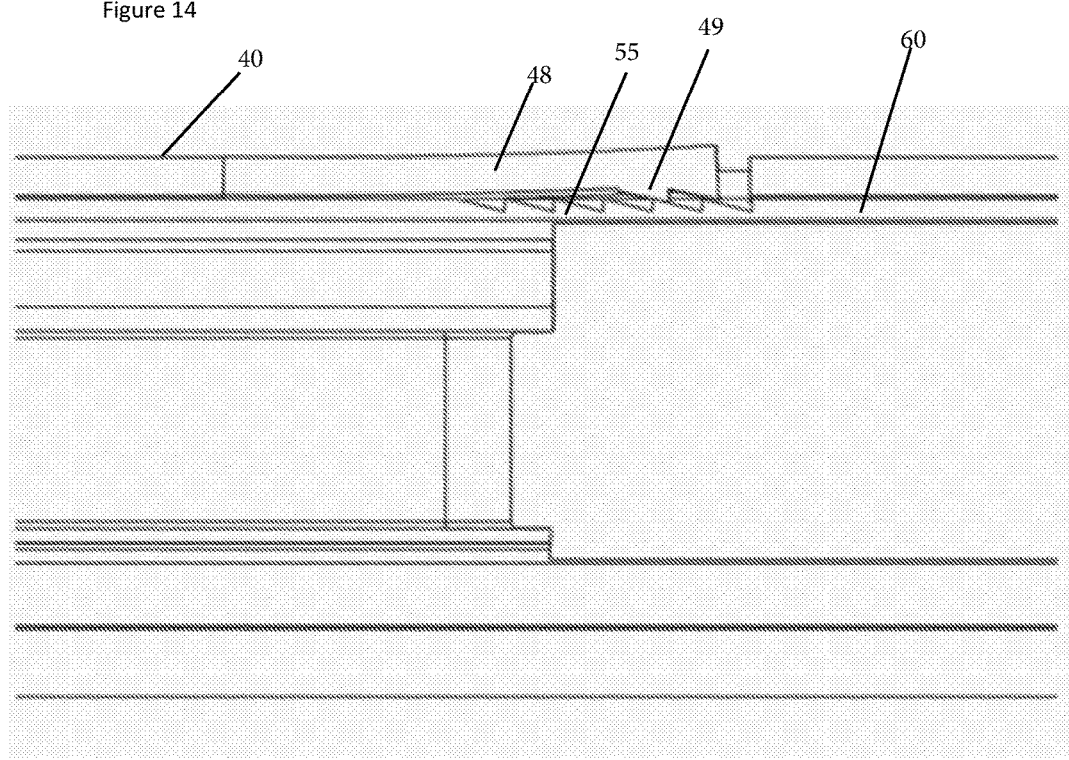
FIG. 31 is a detailed view of the ratchet mechanism to prevent movement of the outer tube towards the handle relative to the inner tube.

A separate mechanism, involving ratchet teeth 55 on inner tube 60, and corresponding projections on outer tube 40 (not shown) prevents backward, that is towards the handle 20. Referring to FIG. 31, ratchet teeth 55 can be seen associated with inner tube 60. Outer tube 40 includes a tongue 48 (see FIGS. 1 and 2), with downward projecting teeth 49. Tongue 48 can flex relative to outer tube 40. As the outer tube is pushed away from handle 20, the teeth 49 engage teeth 55 and backwards movement is prevented. It will be appreciated that a variety of different non-return mechanisms are known and could be used, including providing a series of such ratchets, or a progressive series of such ratchets, or even simple ramp and projections.

Thus, it can be seen that the each operation of trigger 62 moves the outer tube further out by an increment defined by the ratchet teeth 80, and thereby deploys a band.

Figure 8:
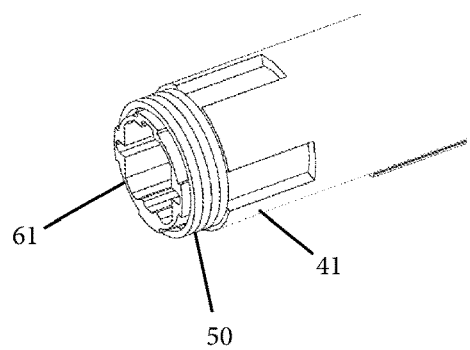
FIG. 8 is a view of a detail of the tip according to an implementation of the invention.
Figure 9:
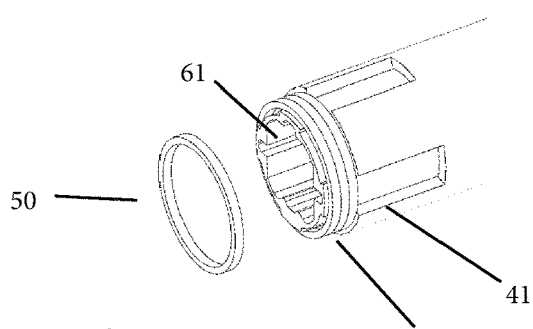
FIG. 9 is a view of a detail of the tip of FIG. 7, with on band having been deployed.

FIGS. 8 and 9 illustrate the band deployment. In FIG. 7, 4 bands 50 are in place on tip 61, with leading edge 41 barely engaging the rear band 50. In FIG. 9, one band 50 has been deployed, or ejected. The remaining bands 50 have been pushed further towards the tip 61. It will be appreciated that in use, as the haemorrhoid has been gripped by grasper 32, and withdrawn into the inner tube 60, the band will locate around the haemorrhoid, preferably near the base.

Thus, the first stage of the procedure, the gripping of the haemorrhoid, may be achieved by movement of the device 10 to the desired haemorrhoid. The physician is then able to position the open grasper 32 on the haemorrhoid as desired. The operator then closes the grasper by operating handle 31, to grip the haemorrhoid, and can exert a gentle pulling force on it. A band 50 can then be deployed by operating trigger 62, to complete the procedure. It will be appreciated that the bands are held in an extended position, and when released will contract to a smaller diameter. In practice, the release is around a haemorrhoid, and when released band 50 will contract and so exert a force around the base of the haemorrhoid, resulting ultimately in its removal.

It will be understood that the trigger arrangement described is merely one convenient form, and any kind of handle or lever associated with the grasper 32 can be used to open and close the grasper 32. The arrangement shown is simple to use and manufacture$_{[RS1]}$. However, it is envisaged that a more complex system, for example using multiple components, could be used to form or move grasper 32. It is also envisaged that other mechanisms could be used to replace link 66 and the related pivoting connections, for example using a live hinge system, connected all the way from trigger 31 to grasper 32.

Figure 12:
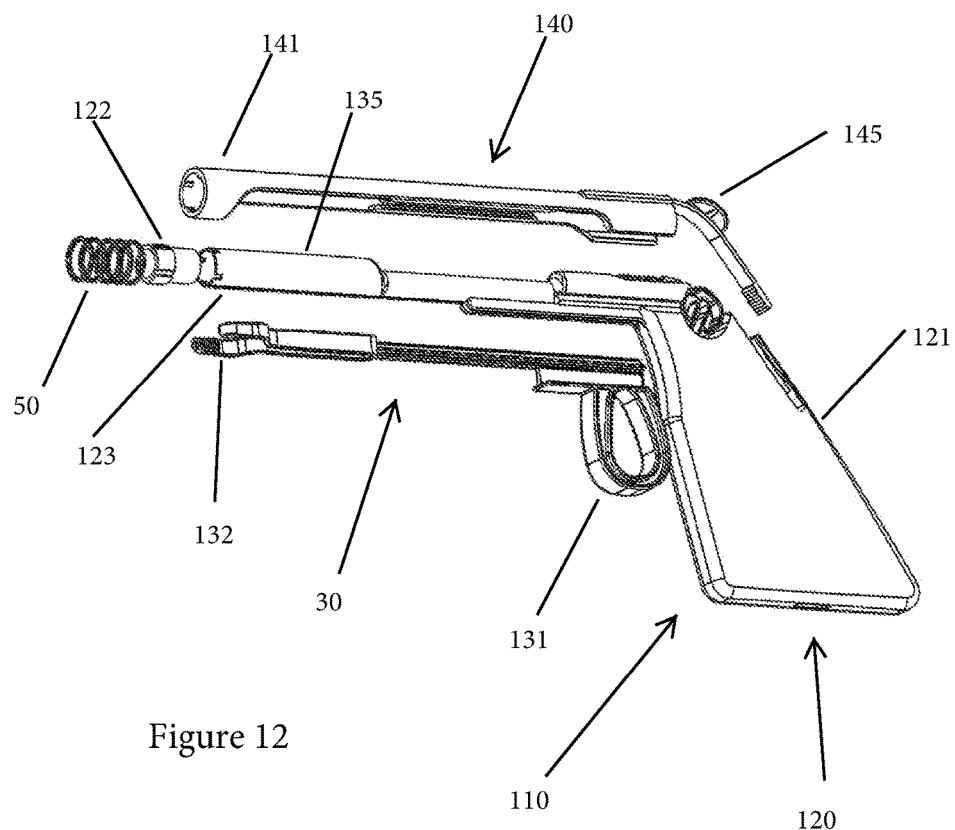
FIG. 12 illustrates an alternative implementation of the present invention.

FIG. 12 illustrates a second implementation, in which rather than the grasper being fixed to the body of the device, the grasper 132 is movable and the tube structure 135 is fixed to the body. Device 110 has a handle 120, with the grasper 132 mounted to a shaft 130 and operating handle 131. It is arranged to slide inside tube 135 and thereby open and close grasper 132, in a similar manner to the first implementation. However, the whole body has to be moved back relative to grasper 132 once it is placed over a haemorrhoid.

In this implementation, the bands 150 are similarly pushed from tip 122, by a deployer structure 140. The deployer structure 140 surrounds the tube structure 135, so that operatively edge 141 pushes bands from tip 122. Operation of button 145 actuates a walking ratchet arrangement, which incrementally moves the deployer structure forward.

Figure 13:
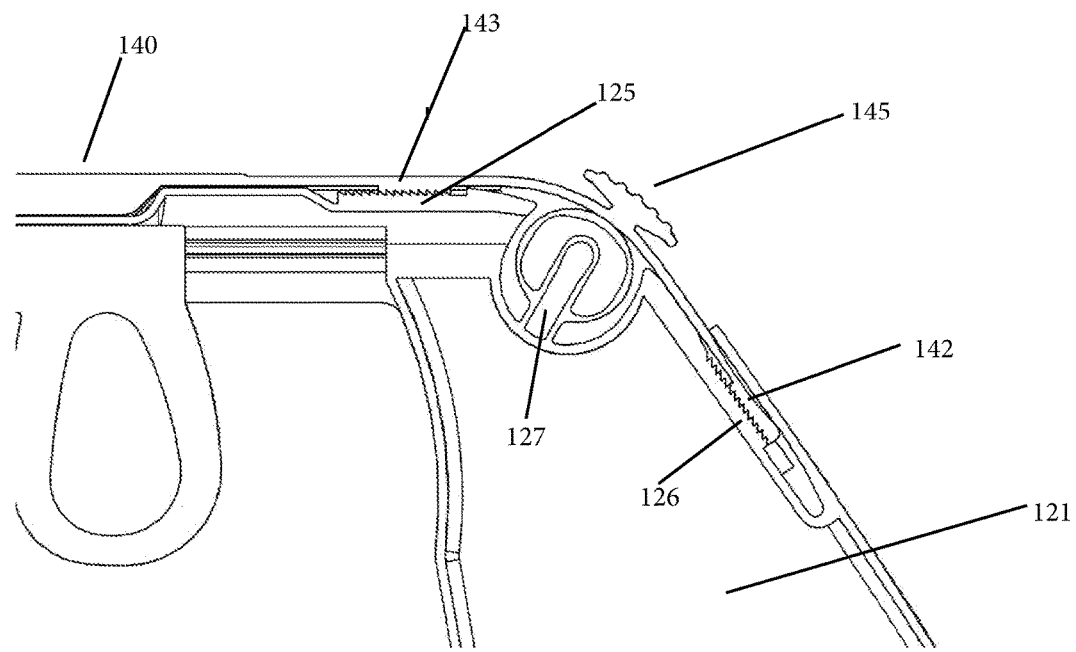
FIG. 13 illustrates a detailed view of an alternative implementation of a trigger mechanism for releasing bands

FIG. 13 illustrates the operation of button 145 and the associated mechanism. According to this implementation, the movement of deployer 140 with respect to body 120 is controlled in a specific way, using a ratchet mechanism. Ratchets 126, 125 on body 120 are engaged by corresponding ratchets 142, 143. The angles on the teeth are such that the movement can only be one way, so that deployer 140 moves out, away from the trigger, so as to force bands 150 to be dispensed from tip 122 as described above.

Button 145 is part of deployer 140, but is supported by a resilient structure 127 moulded into body 120. When button 145 is depressed, the deployer 140 flexes, causing ratchet 143 to walk (to the left in the drawing) relative to ratchet 125, and hence body 120. The angles on the ratchet teeth 126, 142 are such that the deployer can only move towards the tip, any reverse movement is prevented.

When button 145 is released, the resilient structure 127 pushes button 145 back, teeth of ratchet 142 walk over the teeth of ratchet 126, pulling the deployer 140 forward, and into the next incremental position relative to the body 120. The movement is one ratchet tooth, so that the distance moved by deployer 140 is very precisely controlled to only deploy one band 150. Pressing the button again will deploy a further band.

These implementations include pre-loaded bands, for the convenience of the physician. However, in other implementations the bands, or additional bands, may be loaded at the point of treatment.

Figure 14:
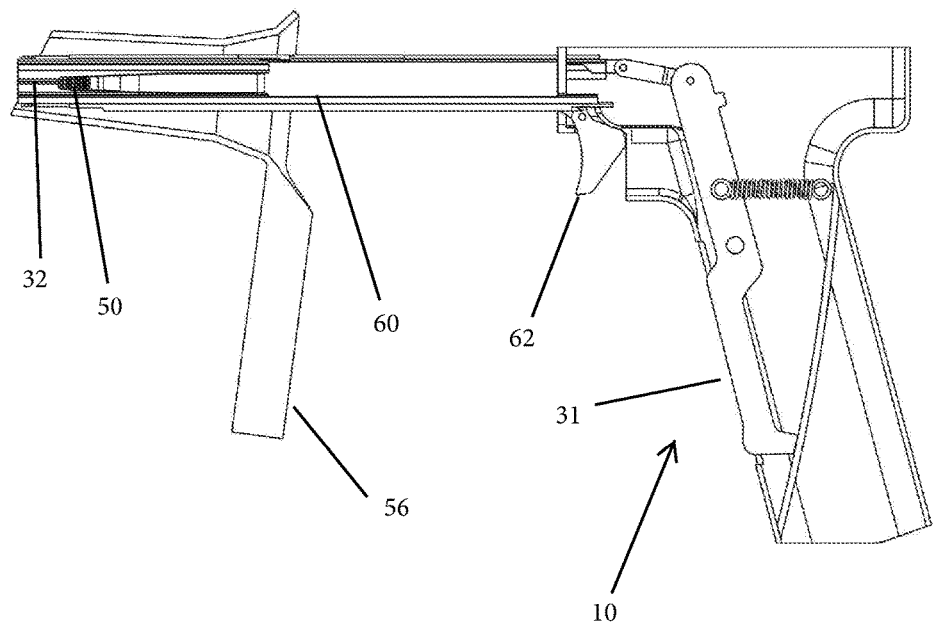
FIG. 14 illustrates the use of an implementation of the present invention with an anoscope.

FIG. 14 illustrates the use of the ligature device 10 with an anoscope 56. The anoscope 56 is inserted through the anus of the patient in a conventional manner, as with existing procedures. The device 10, with grasper 32 open or closed as desired, is inserted into anoscope 56. The physician identifies a candidate haemorrhoid. Grasper 32 is opened and placed over the haemorrhoid, and handle 31 operated to grip it, drawing the grasper and haemorrhoid into the inner tube 60. Operation of trigger 62 then deploys a band 50 around the haemorrhoid.

Although we have referred to anoscope, it will be apparent that the present invention may be employed with other suitable devices, for example proctoscopes.

Figure 10:
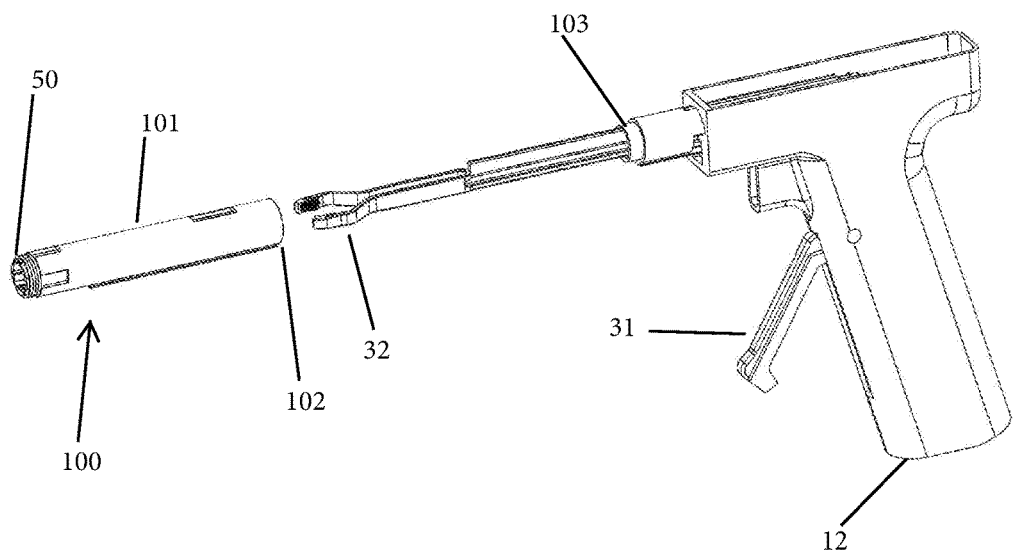
FIG. 10 illustrates another implementation, with a removable tip.

FIG. 10 illustrates a structure similar in operation to FIG. 1, but in which the device 12 has a removable tip, for example for use as a re-usable main device 12 with a disposable section 100. Section 100 has re-loaded bands 50, and a tip section 101, and in use the grasper 32 projects through structure 100. Base 102 mates with base 103, in order to provide a connection between the inner tube of the section and the inner tube of device 12. So long as the inner tube is connected, for example by a bayonet or other removable connection, it is possible that no connection is required for the outer tube, as it is simply pushed relative to the inner tube for band release.

Figure 11:
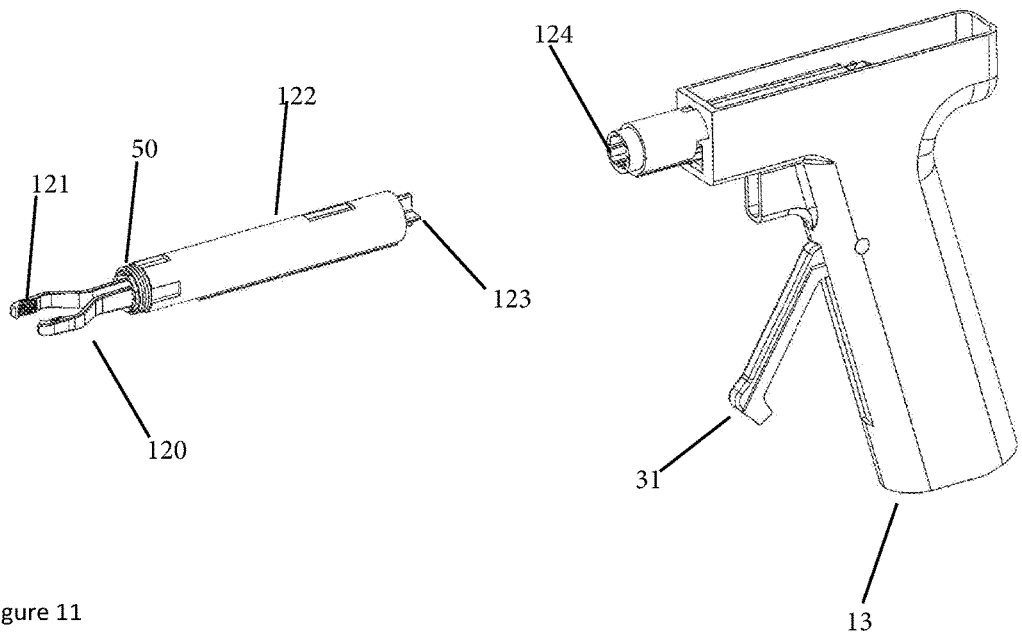
FIG. 11 illustrates another implementation with a removable tip.

FIG. 11 illustrates another structure with a removable component. In this case, device 13 is adapted to connect to component 120, which includes not only the bands 50 and tip, but also grasper 121. In this case, both the grasper 121 must connect by shaft 123 to main device 124, as well as the inner and optionally outer tube to allow for release of bands and grasper 121 operation.

An alternative structure for incremental movement of the outer tube 40 relative to the inner tube 60, so as to release bands 50 on command, and one at a time, will now be described with reference to FIGS. 15 to 30. In general terms, this mechanism uses two different notches for engagement by a tooth on the trigger, as well as flexible prongs located inside a pair of cams which progressively deploy to create incremental movement of the outer tube 40.

Figure 15:
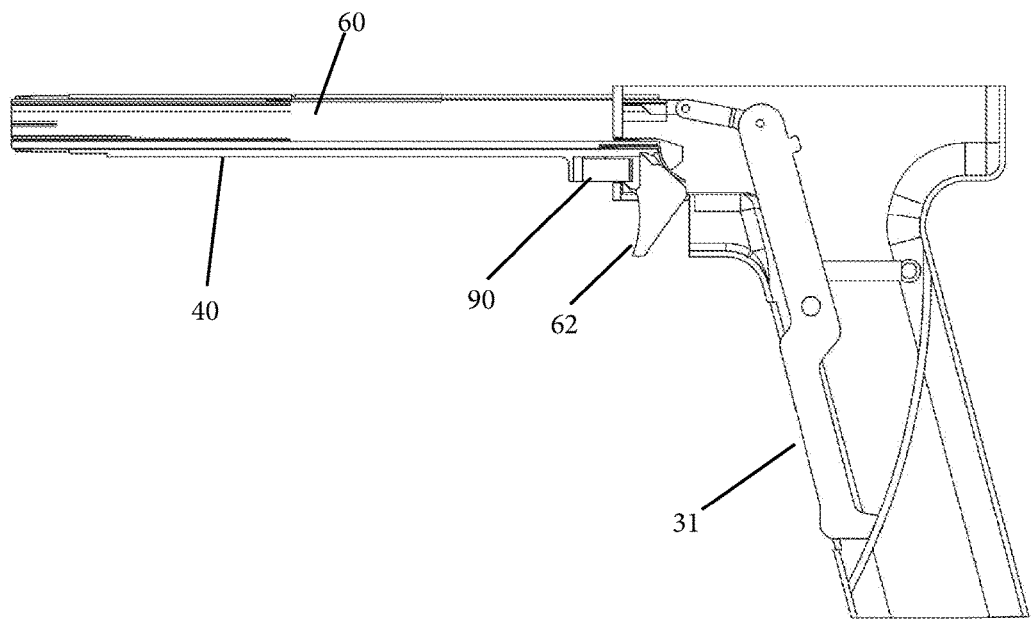
FIG. 15 is a side view, in section, of a further embodiment of the invention.

In FIG. 15, the overall structure can be seen. The bands are deployed by movement of the outer tube 40 over the inner tube 60, as in the other example. As such, this aspect will not be discussed. As in the other example, a ratchet or similar structure is provide between the inner and outer tubes to prevent backwards movement. Again, as this is identical in principle, this will not be described further.

Figure 16:
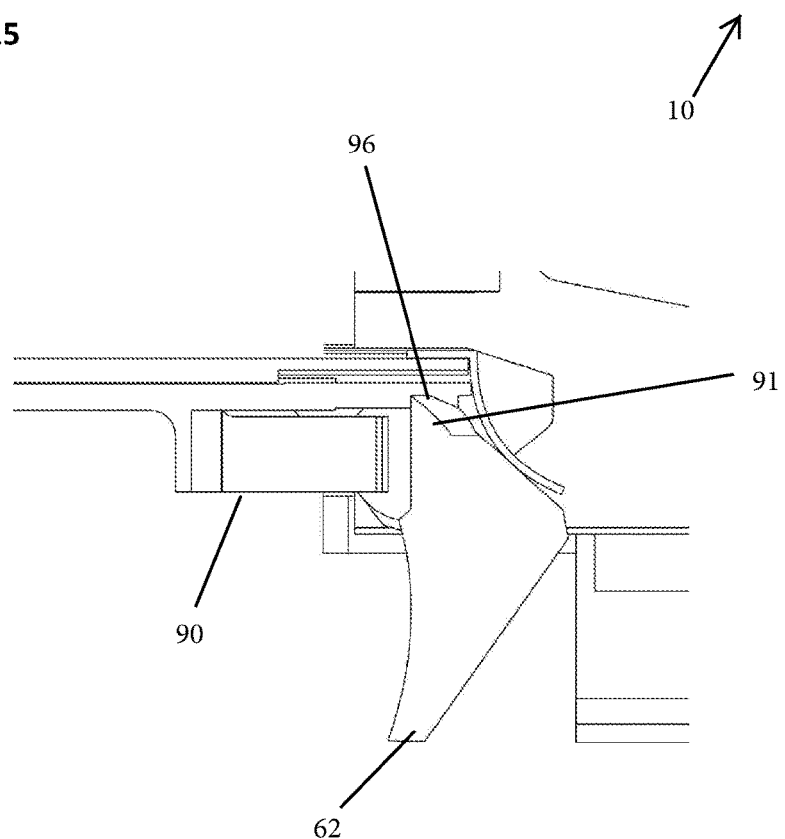
FIGS. 16, 18, 21, 23, 25, 26 and 29 are detailed section views illustrating different stages of a band release trigger mechanism.
Figure 17:
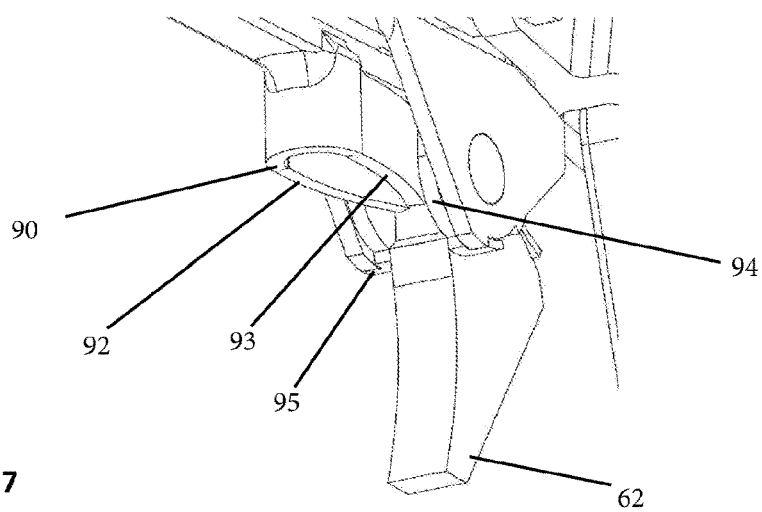
FIGS. 17, 19, 20, 22, 24, 27 and 30 are detailed isometric views of different stages of a band release trigger mechanism.

The mechanism, however, for trigger 62 is quite different. The most obvious difference is the presence of prong structure 90. Referring to FIGS. 16 and 17, these show the mechanism before any bands are deployed. Tooth 91 of trigger 62 is located in notch 96. Prongs 92, 93 are connected to outer tube 40 and are received inside cams 94, 95 which are effectively inside trigger 62. Notches 96, 97 are located on projection 98, which flexes as the trigger 62 and tooth 91 move past it.

Figure 18:
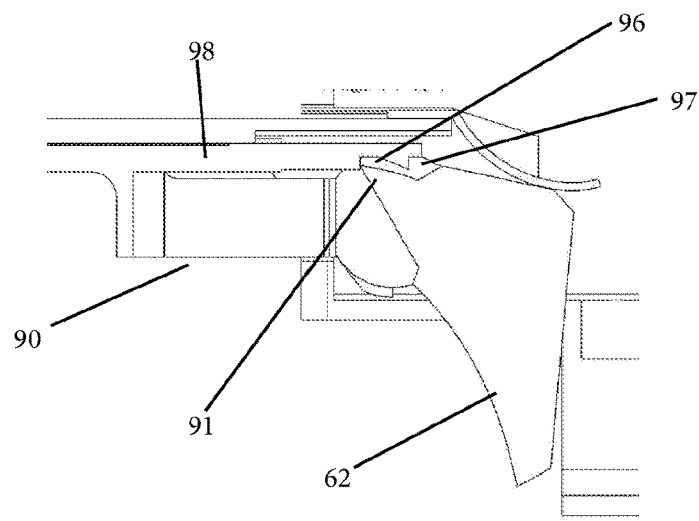
Figure 19:
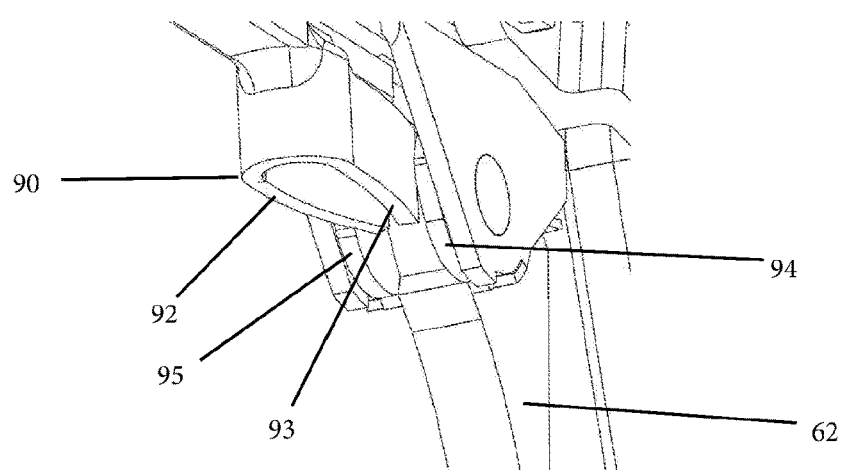

In FIGS. 18 and 19, the trigger has been depressed to deploy the first band. Tooth 91 has pushed notch 96 so that the outer tube 40 has been displaced forward. Prongs 92, 93 remain within the cams 94, 95.

Figure 20:
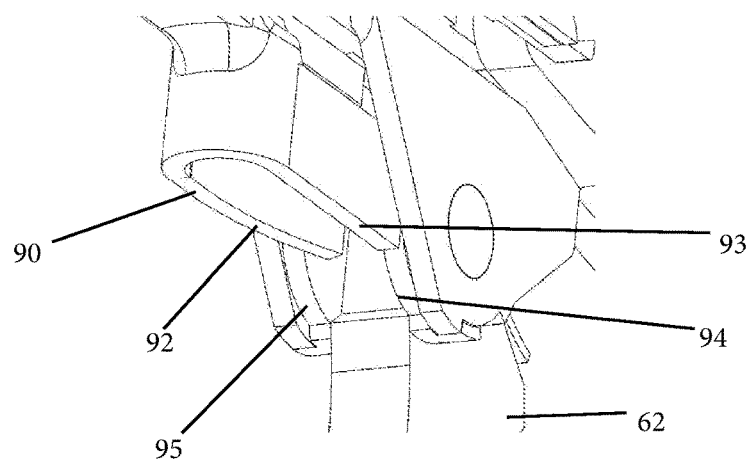

FIG. 20 illustrates the situation after the trigger is released, in which because the outer tube 40 has moved, prong 93 is now able to flex out and is located on cam 94. Prong 92 is still too long to deploy, and remains inside cams 94. 95.

Figure 21:
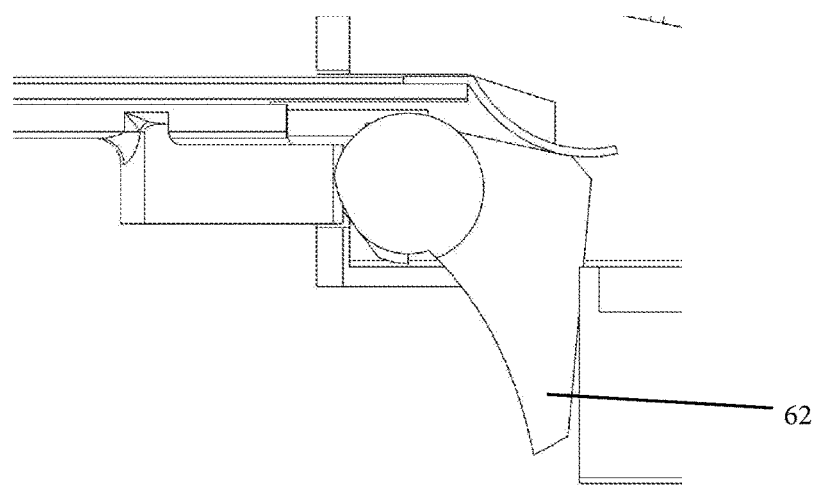
Figure 22:
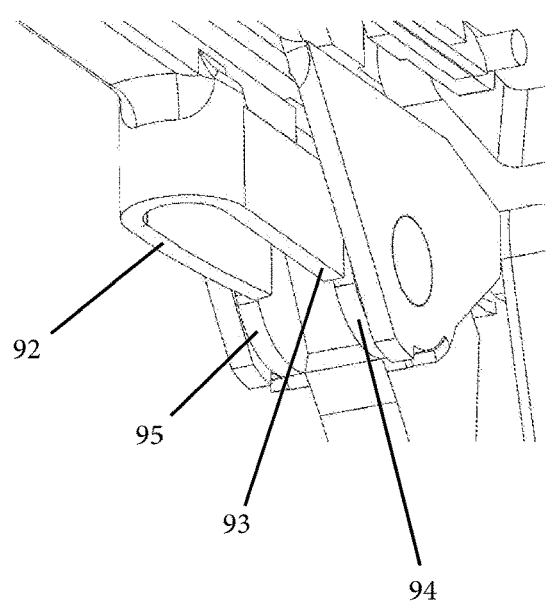

When the trigger is depressed again, shown in FIGS. 21 and 22, prong 93 is engaged by cam 94 and pushes the structure forward, to deploy a second band.

Figure 23:
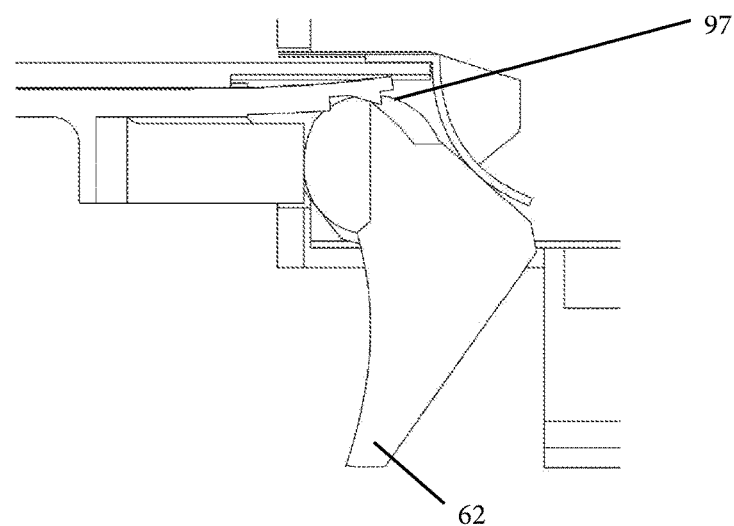
Figure 24:
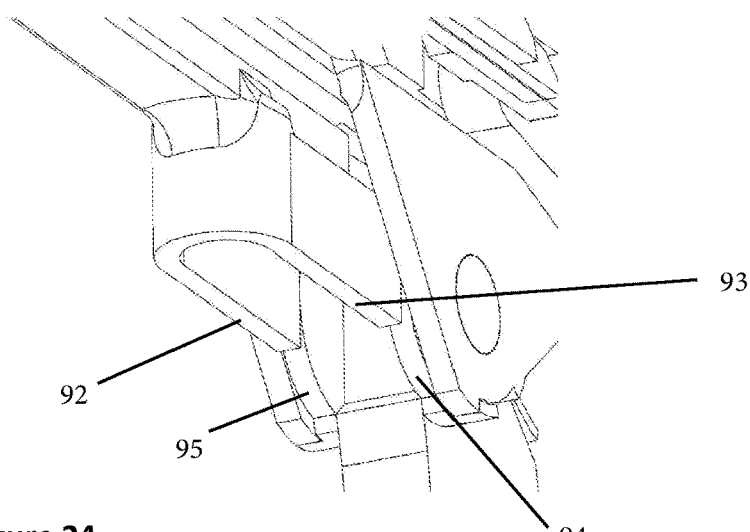

FIGS. 23 and 24 illustrate the situation after the trigger is released, and the mechanism is now ready to deploy the third band. Prong 92 can now deploy, as the structure has moved further, and engages cam 95. Note, the previous movement was large enough such that prong 93 is no longer engaged.

Figure 25:
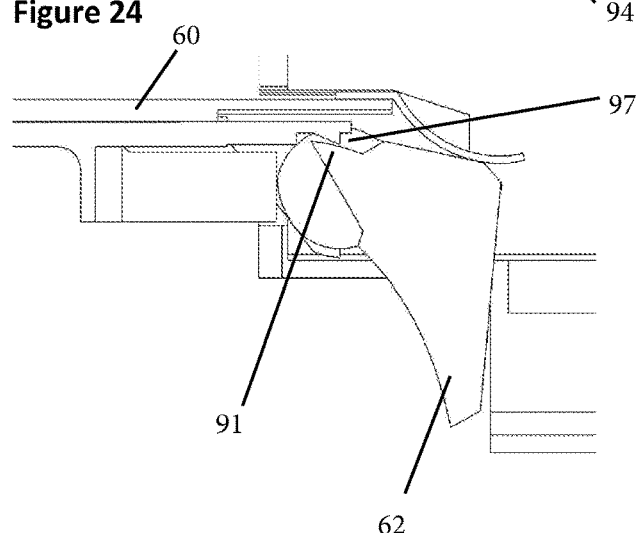

FIG. 25 illustrates that trigger 62 has been depressed to deploy the third band. Note, at this stage tooth 91 is not able to engage notch 97. Prong 92 pushes the structure forward by engaging with cam 95, and the third band is deployed.

Figure 26:
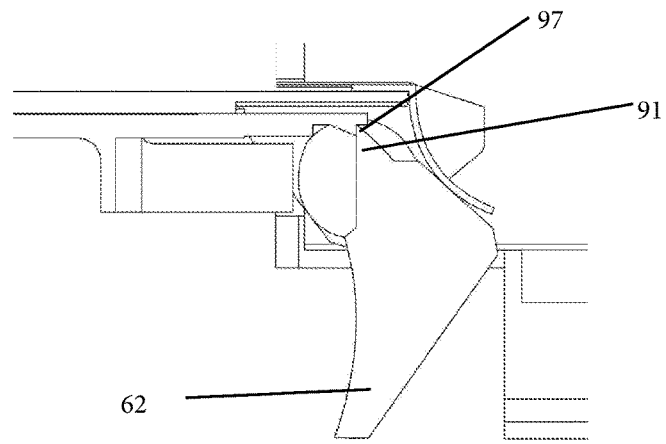
Figure 27:
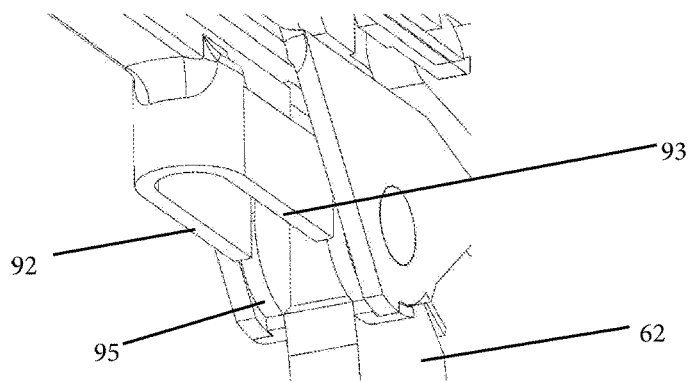

FIGS. 26 and 27 show the trigger released and ready for deployment of the fourth band. Note, the tooth 91 is now engaged with notch 97. Neither of the prongs 92, 93 are engaged, as the structure has moved too far forward.

Figure 28:
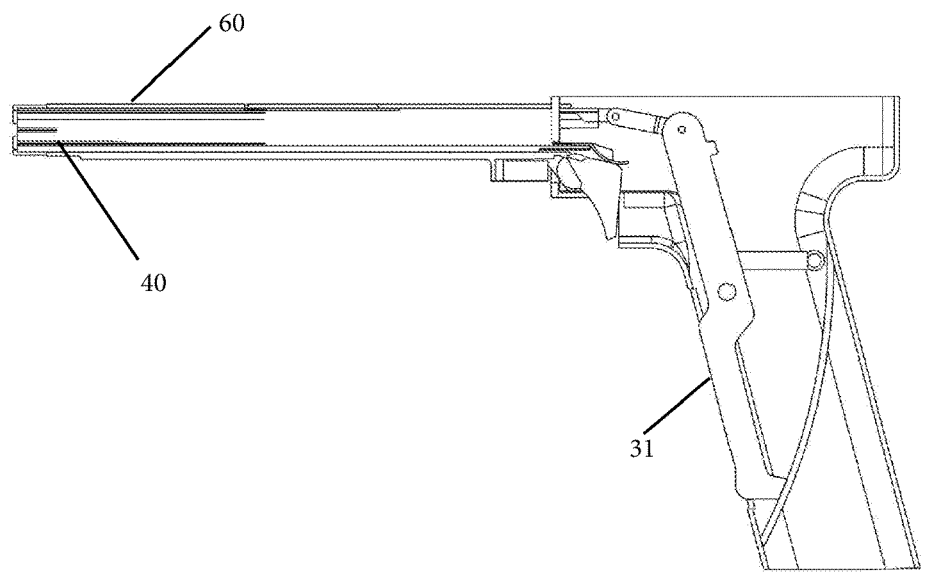
FIG. 28 is a view, in section, of the embodiment of FIG. 15, but with further bands deployed and greater relative movement between the inner and outer tubes.
Figure 29:
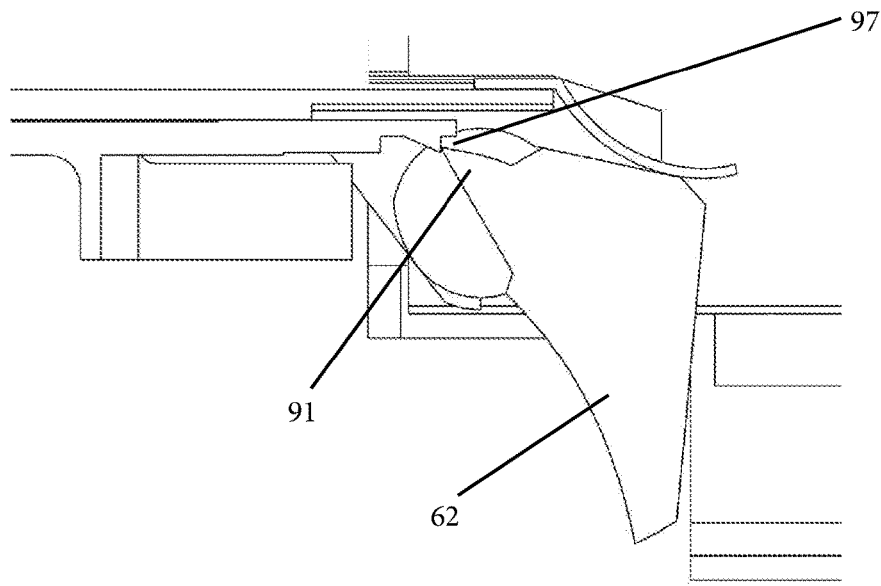
Figure 30:
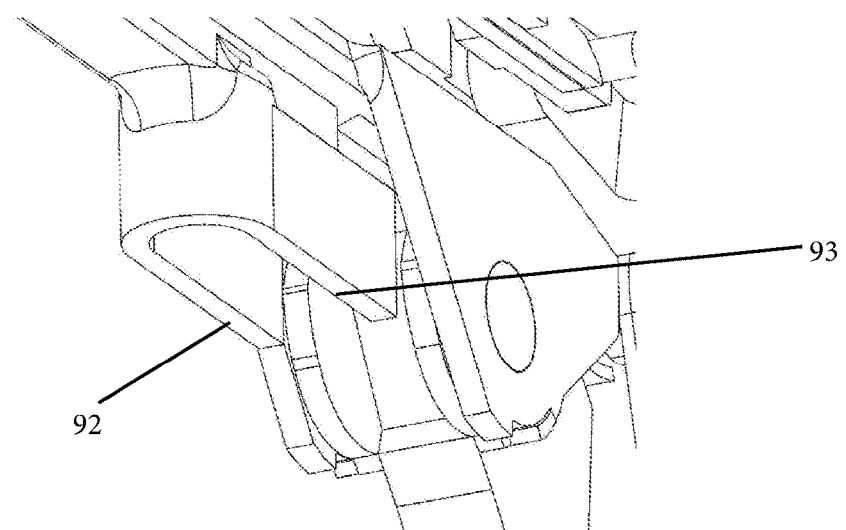

FIGS. 28, 29 and 30 illustrate the deployment of the last band. From a comparison of FIGS. 28 and 15, the relative movement of outer tube 40 and inner tube 60 can be seen. Tooth 91 engages notch 97 and thereby deploys the last band.

The entire structure may be constructed from a suitable plastic material, for example polycarbonate, ABS, polypropylene, or any other suitable material, or mixtures of such materials for different components. In non-disposable implementations, more durable materials, for example stainless steel, may be used. The parts may be formed by injection moulding or any other suitable procedure. The body section may be formed from a single component, or from 2 or more parts that are joined. It will be appreciated that depending upon the materials and manufacturing process selected, the device may be formed from different numbers of components to create the final assembly, compared to the examples provided.

The described implementations of the present invention allow for the operator, using a single hand, to control the gripping of the haemorrhoid with a manual device, not requiring suction. At the same time, with the same hand, the operator can deploy multiple bands, one at a time, with a simple trigger mechanism. This provides significant advantages for the physician in performing the banding procedure.

It will be appreciated that the terms handle and trigger are intended in the broad sense, as mechanical releases in the broadest sense. They can operate by pivoting, sliding, rotating, depression or any other convenient mechanical arrangement, in order to initiate the desired function.

It will be appreciated that various aspects of the implementation may be varied in different implementations of the invention. For example, the deployer could be moved to a different position on the body. A different mechanism may be used to control dispensing of bands.

The disclosure of all references cited herein are hereby incorporated by reference, as is the complete disclosure of the Australian provisional application No. 2015905345 by the present applicant.

The invention claimed is:

1. An elastic band ligation device adapted for one handed operation, the device including:
   a grasper including at least two gripping arms slidably located within a tube wherein movement of the grasper out of the tube causes the gripping arms to open and movement of the grasper into the tube causes the gripping arms to close;
   a handle and a manually operable member moveably coupled to the handle, the handle and the manually operable member being operable with one hand for positioning the grasper relative to a haemorrhoid and slidably moving the grasper relative to the tube for closing the gripping arms to retain the haemorrhoid and drawing the gripping arms and the haemorrhoid into the tube;
   a plurality of bands located at an end of the tube and a deployment mechanism operable by consecutive movements with the one hand for consecutively advancing a band deployment member incrementally relative to the tube for deploying consecutive bands from the end of the tube,
   wherein the deployment mechanism includes a ratchet drive mechanism wherein movement of the manually operable member relative to the handle causes the ratchet drive mechanism to advance the band deployment member incrementally relative to the tube.

2. The device of claim 1, wherein the deployment mechanism is operable with the same hand without removing the hand from the handle for deploying consecutive bands.

3. The device of claim 1, wherein the deployment mechanism includes a non-return mechanism to prevent inadvertent retreat of the band deployment member relative to the tube.

4. The device of claim 1, wherein the ratchet drive mechanism includes an arrangement of interengaging teeth between the tube and the band deployment member.

5. The device of claim 1, wherein the ratchet drive mechanism includes a cam and a follower arrangement.

6. The device of claim 5, wherein movement of the manually operable member relative to the handle causes rotation of the cam, wherein rotation of the cam displaces the follower causing the advancement of the deployment member.

7. The device of claim 1, wherein the deployment mechanism includes a biasing spring exerting a force that must be manually overcome to advance the deployment member relative to the tube.

8. The device of claim 1, wherein the gripping arms interact with an inner surface of the tube in order to close the gripping arms, the gripping arms being resiliently biased open.

9. The device of claim 1, wherein the deployment mechanism includes a trigger having an active condition in which the trigger is operable by the same hand without removing the hand from the handle for advancing the band deployment member.

10. The device of claim 9, wherein the trigger assumes the active condition by operation of the movement of the manually operable member relative to the handle to draw the gripping arms and the haemorrhoid into the tube.

11. The device of claim 9, wherein the trigger has an inactive condition in which the trigger is contained within the handle and the trigger emerges from within the handle when assuming the active condition.

12. The device of claim 9, wherein the trigger is operable each time the trigger is fully depressed to deploy one band and when released is reset to deploy a successive band.

* * * * *